United States Patent [19]

Jannssen

[11] 4,384,912

[45] May 24, 1983

[54] VISIBLE INDEXES

[76] Inventor: Alexander P. Jannssen, 28 Old Farm Rd., Bellair, Charlottesville, Va. 22901

[21] Appl. No.: 306,722

[22] Filed: Sep. 29, 1981

Related U.S. Application Data

[60] Division of Ser. No. 228,356, Jan. 26, 1981, Pat. No. 4,347,274, which is a continuation-in-part of Ser. No. 30,458, Apr. 16, 1979, Pat. No. 4,250,216, which is a continuation of Ser. No. 795,882, May 11, 1977, abandoned, which is a division of Ser. No. 505,078, Sep. 11, 1974, abandoned.

[51] Int. Cl.[3] ...................... B32B 31/00; A61F 13/02; B32B 3/10

[52] U.S. Cl. .................................... 156/277; 40/2 R; 428/40; 428/41; 428/42; 428/54; 428/78

[58] Field of Search .................. 156/277, 157; 428/40, 428/42, 43, 54, 78, 41; 40/2 R

[56] References Cited

U.S. PATENT DOCUMENTS

| | | | |
|---|---|---|---|
| 1,960,137 | 5/1934 | Brown | 428/40 |
| 2,832,712 | 4/1958 | Deinlein et al. | 40/2 R X |
| 3,226,862 | 1/1966 | Gabruk | 428/42 X |
| 3,352,740 | 11/1967 | Fleischhauer | 428/43 |
| 3,674,614 | 7/1972 | Templeton | 428/43 |
| 3,841,934 | 10/1974 | Rasborough et al. | 156/157 |
| 4,024,302 | 5/1977 | Takagi et al. | 156/157 X |
| 4,078,109 | 3/1978 | Kando et al. | 428/54 X |
| 4,087,310 | 5/1978 | Schmidt | 156/157 X |

*Primary Examiner*—Thomas J. Herbert, Jr.
*Attorney, Agent, or Firm*—LeBlanc, Nolan, Shur & Nies

[57] ABSTRACT

Visible index strip rolls of a novel, cost effective construction; and methods and machinery for manufacturing those rolls.

7 Claims, 6 Drawing Figures

VISIBLE INDEXES

The present application is a division of application Ser. No. 228,356 filed Jan. 26, 1981, now U.S. Pat. No. 4,347,274. The latter is a continuation-in-part of application Ser. No. 30,458 filed Apr. 16, 1979 (now U.S. Pat. No. 4,250,216 issued Feb. 10, 1981); and application Ser. No. 30,458 is a continuation of application Ser. No. 795,882 filed May 11, 1977 (now abandoned). Application Ser. No. 795,882 is a division of application Ser. No. 505,078 filed Sept. 11, 1974 (now abandoned).

This invention relates to the display of information and, more particularly, to information display systems of the visible index type.

Visible indexes have seen widespread use for many years. Such indexes typically include a stand to which a number of frames or supports can be attached. These frames consist of a strip supporting panel extending between side members having recesses into which the ends of narrow, elongated, flexible index strips bearing wanted information can be inserted to detachable secure the strips in place.

The index strips can consequently be readily removed and replaced or relocated, making it relatively easy to keep the index current. At the same time the information is available in a highly accessible form.

The index strips for systems of the type just described have heretofore mostly been made of paper covered wood veneer. They are typically secured to a backing sheet to facilitate handling and the typing or other machine printing of the wanted information on them. They are then separated for attachment to the frame or support by rupturing the backing sheet or detaching them from it.

A number of patents deal with visible index systems and the index strips used in such systems. Among these are U.S. Pat. Nos. 499,442 issued June 13, 1893; 1,123,215 issued Jan. 5, 1915; 1,183,370 issued May 16, 1916; 1,185,538 issued May 30, 1916; 1,227,661 issued May 29, 1917; 1,244,622 issued Oct. 30, 1917; 1,285,760 issued Nov. 26, 1918; 1,329,568 issued Feb. 3, 1920; 1,462,497 issued July 24, 1923; 1,504,709 issued Aug. 12, 1924; 1,511,750 issued Oct. 14, 1924; 1,518,354 issued Dec. 9, 1924; 1,525,079 issued Feb. 3, 1925; 1,529,212 issued Mar. 10, 1925; 1,554,087 issued Sept. 15, 1925; 1,589,556 issued June 22, 1926; 1,594,112 issued July 27, 1926; 1,695,328 issued Dec. 18, 1928; 1,574,931 isued Mar. 2, 1926; 1,774,241 issued Aug. 26, 1930; 1,809,066 issued June 9, 1931; 1,854,807 issued Apr. 19, 1932; 2,058,034 issued Oct. 20, 1936; 2,201,950 issued May 21, 1940; 2,385,082 issued Sept. 18, 1945; 2,529,926 issued Nov. 14, 1950; 2,574,068 issued Apr. 3, 1951; 2,522,270 issued Sept. 8, 1953; and 2,732,822 issued Jan. 31, 1956.

Initially, and still commonly, the index strips are supplied in sheet form with each sheet including a number of index strips. The wanted information is printed on the strips by hand or by a typewriter or the like; and the strips are then torn apart or peeled off the backing sheet to separate them as pointed out above the fitted into the supporting frame.

More recently, it has become desirable to print the wanted information on the strips faster than can be done by hand or with a typewriter, and machines capable of reaching that goal have been made available. Insofar as I am aware, these machines require that the index strips be made available in roll form and that there be serially spaced perforations along the edges of the roll which can be engaged by a registration device of the printing machine to insure that wanted information is properly placed on the index strips.

By an index strip roll I mean a construction which includes index strips extending transversely relative to a backing which is sufficiently flexible that the assemblage of strips and backing can be wound or otherwise formed into a roll having a length that considerably exceeds its span.

One index roll developed for the purposes identified above is described in U.S. Pat. Nos. 2,832,712 issued Apr. 29, 1958, to Deinlein and 3,352,740 isued Nov. 14, 1967, to Fleischhauer. It consists of index strips made of wood veneer faced with paper and united by a thin backing sheet that can be ruptured to separate the strips. Registration holes are punched at intervals along the edges of the roll, and it is scored through inwardly of these holes to the backing sheet so that the marginal portions of the roll containing the holes can be broken off after the wanted information has been printed on the index strips. Individual strips are separated by similarly rupturing the backing sheet.

Perhaps the major disadvantage of this just described index roll is that is is economically unattractive under presently existing conditions. Specifically, wood veneers are currently in demand and accordingly command high prices. Yet, one recently examined, currently commercially available index strip roll with eight inch long strips of the type just described had marginal portions totalling one and one-eighth inches in length that are discarded. Thus, over 13 percent of the veneer is wasted in using the strips.

Other disadvantages of the heretofore available index strip constructions described above are that ragged edges are left on the edges and the ends of the strips when the marginal portions are detached and the strips are separated and that fibers may be torn from the backing and adhere to the strip when they are detached. In those cases where the strips are separated by removing them from a backing sheet, the torn material and ragged edges are unsightly, an extremely important disadvantage from the commercial viewpoint. Also, adhering backing sheet material can keep the strips from being spaced as closely together in a frame as is desirable.

I have since developed an improved visible index strip roll based on the sheet type index strip assmeblages disclosed in copending application Ser. No. 30,458. Those assemblages include a plurality of elongated, flexible index strips bonded to a backing sheet by a releasable adhesive (a releasable adhesive is one which forms with the backing sheet and with the index strips a bond stronger than the adhesive itself so that the adhesive will rupture internally rather than one of the adhesive to paper bonds rupturing when an index strip is detached from the backing sheet).

As a consequence of using a releasable adhesive, the edges of the strip are clean rather than ragged as has heretofore too often been the case; and backing sheet material is not apt to be removed with an index strip when the latter is detached from the backing sheet.

The index strips of such assemblages are preferably of the novel, multi-ply, all paper construction disclosed in application Ser. No. 30,458 with the core stock being a paper of the character described in U.S. Pat. No. 3,769,143, issued Oct. 30, 1973, to Kulesza which is hereby incorporated by reference. Such papers are composed of a fibrous mat impregnated with a partially cured, resin-modified, cross-lined, urea-formaldehyde resin. The modifier resin is a polymerized, ethylenically unsaturated monomer and contains chain-pendant methylol groups. The urea-formaldehyde contains ca. 1.3 to 2.2 moles of formaldehyde per mole of urea, and the paper contains ca. 25 to 75 percent by weight of the modified urea-formaldehyde resin.

These papers have properties which, for my purposes, surpass those of wood veneers and other papers; and they do not have certain disadvantages appurtenant to these materials. For example, they are harder than wood veneers and are free of knot-holes and irregular grains.

My previously developed index strip rolls were made by butt joining sheet type assemblages of the character just described, perforating the edges of the resulting roll, scoring through its marginal portions inwardly of the perforations to the backing sheet, and then peeling off from the backing sheet and discarding the thus trimmed away ends of the index strips.

This type of visible index strip roll has the advantages that the strips can be detached from the backing sheet without damaging them and that the edges and ends of the strips are sharp and clean rather than ragged like those disclosed in U.S. Pat. Nos. 2,832,712 and 3,352,740. However, there is a waste of material that is economically significant, principally because of the core stock, even though that material is less expensive than the otherwise used wood veneers. Another disadvantage of these nevertheless improved index strip rolls is that specially dimensioned sheets must be employed to accommodate the trimming of the margins; and this noticeably increases manufacturing costs.

I have now invented a new and novel index strip roll construction which has all of the advantages of those I developed earlier but does away with the economically related disadvantages of the latter.

Typically, my more recently developed visible index rolls are made by joining narrow strips or ribbons to opposite margins of butted sheet type index strip assemblages as disclosed in application Ser. No. 30,458 and described above. Adhesively faced flexible tapes are used to join the strips and sheets of strips together and, also, to splice the sheets of strips into a roll. Thereafter, the spliced on strips are perforated to complete the manufacturing process.

This novel construction reduces the wastage of the wood veneer or other core stock and the other materials making up the index strips that is appurtenant to the providing of perforations in my earlier developed index strip rolls. Further, because ends of the index strips are not made unusable in the manufacturing process, the novel index roll constructions I have now invented can be made up from stock sizes of index strip assemblages which is also economically advantageous to a significant extent. And further economies may be realized because at least the heretofore required steps of slitting and peeling off the margins of the roll are eliminated.

I wish to point out, in conjunction with the foregoing, that the use of adhesively faced tapes to butt join sheets of index strips into a continuous roll is not, per se, claimed to be my invention. Indeed, that approach is disclosed in the Deinlein and Fleischauer patents identified above. What those patentees failed to recognize, however, and what I have discovered is that material wastage can be reduced and a significant cost advantage realized by also using those tapes to splice perforatable marginal strips to the sheets of index strips.

It will be apparent to the reader, from the foregoing, that one important and primary object of the present invention is the provision of novel, improved index strips in roll form for information display systems of the visible index type.

Another important, and primary, object of my invention is to provide novel, improved techniques and machinery for manufacturing visible index strip rolls.

Other important and related but more specific objects of my invention reside in the provision of visible index strip constructions:

which reduce the wastage of material incurred in making heretofore available visible index strip rolls;

which are economically advantageous in that they can be made from stock materials;

which have all the advantages of the sheet type visible index strip constructions disclosed in copending application Ser. No. 30,458; and which can be manufactured with a minimum of machinery and in a minimum number of steps.

BRIEF DESCRIPTION OF THE DRAWINGS

Other important objects and features and additional advantages of my invention will become apparent from the appended claims and as the ensuing detailed description and discussion proceeds in conjunction with the accompanying drawings, in which:

DETAILED DESCRIPTION OF THE DRAWINGS

Figure 1:
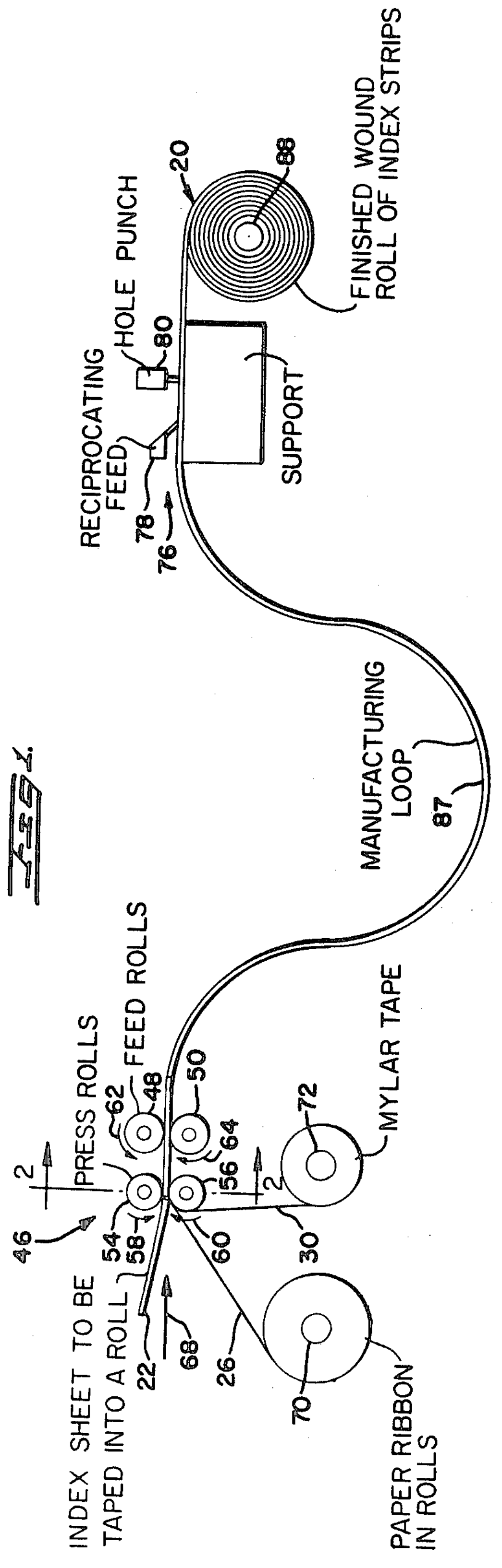
FIG. 1 is a schematic illustration of equipment for manufacturing visible index strip rolls embodying the principles of the present invention.
Figure 2:
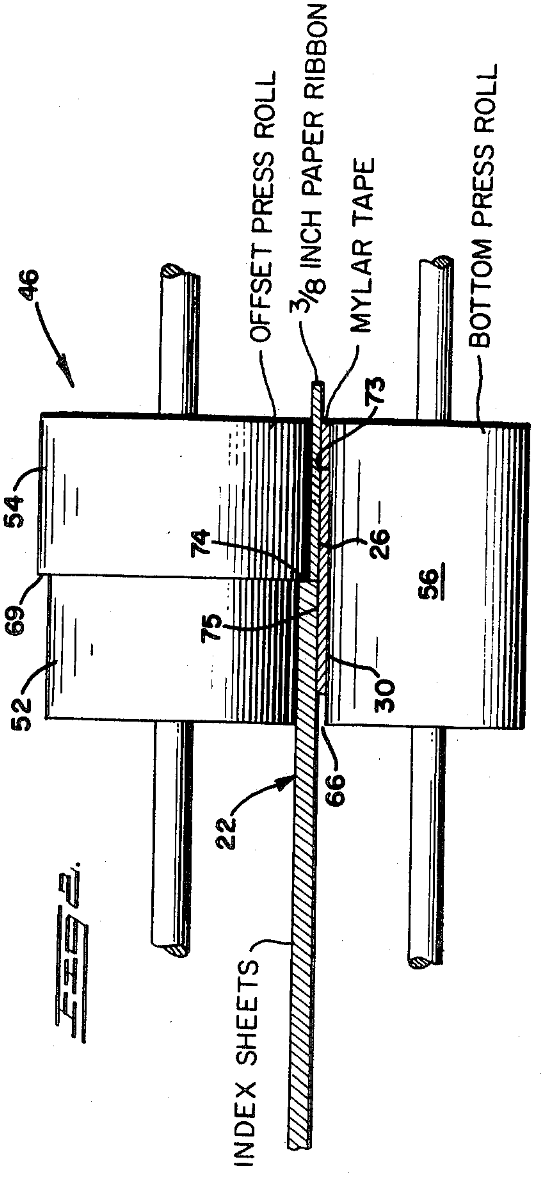
FIG. 2 is a view of the equipment illustrated in FIG. 1 taken substantially along line 2—2 of the latter Figure.

Referring now to the drawings, FIGS. 1 and 2 schematically depict exemplary equipment for manufacturing visible index strip rolls embodying the principles of the present invention. The completed roll 20 is illustrated in FIGS. 3 and 4.

Roll 20 is made up of butted together sheet type visible index strip assemblages 22, preferably of the character disclosed in copending application Ser. No. 30,458, and perforated, flexible strips or ribbons 24 and 26.

Figure 3:
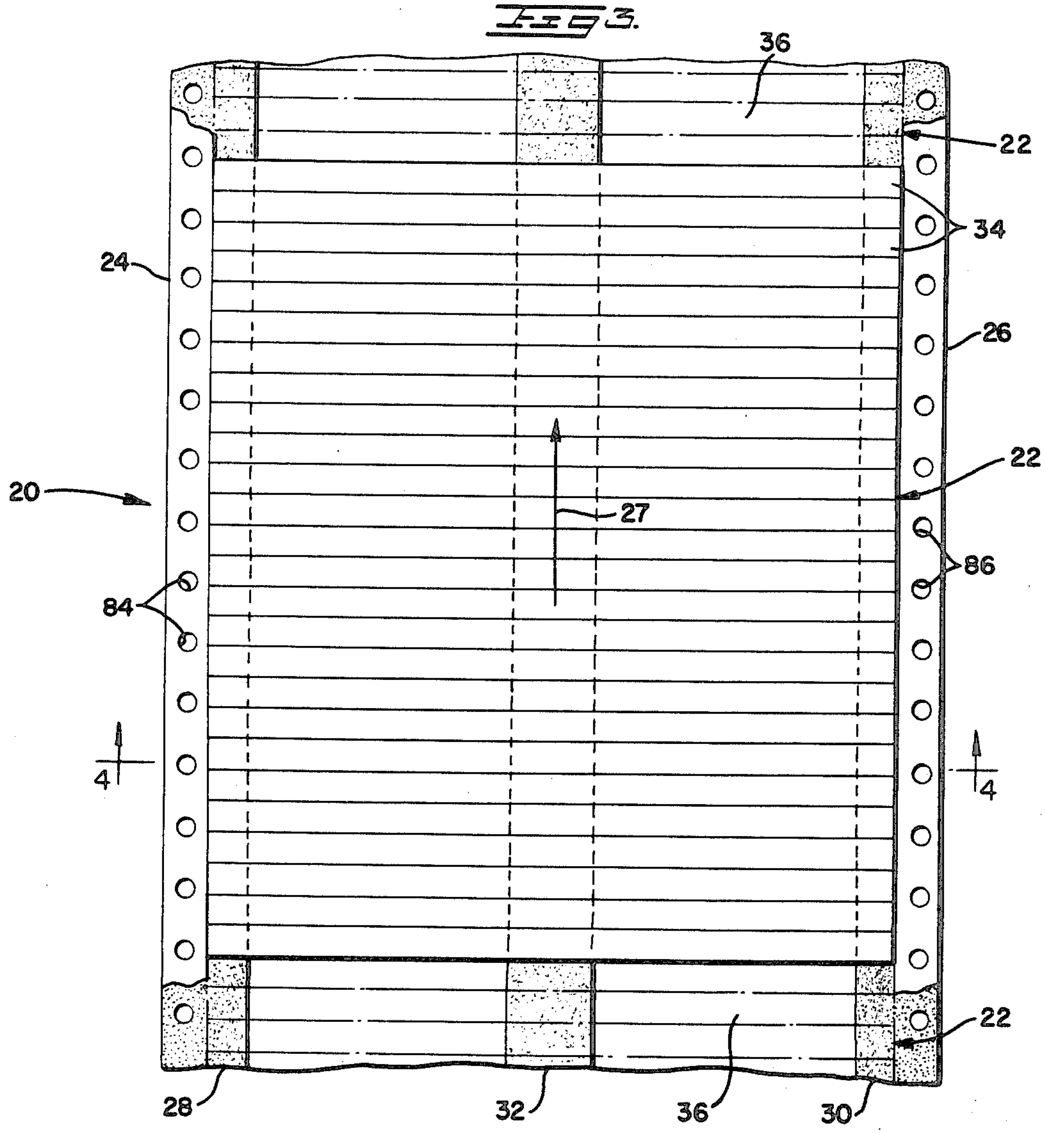
FIG. 3 is a plan view of a visible index strip roll embodying the principles of the present invention.
Figure 4:
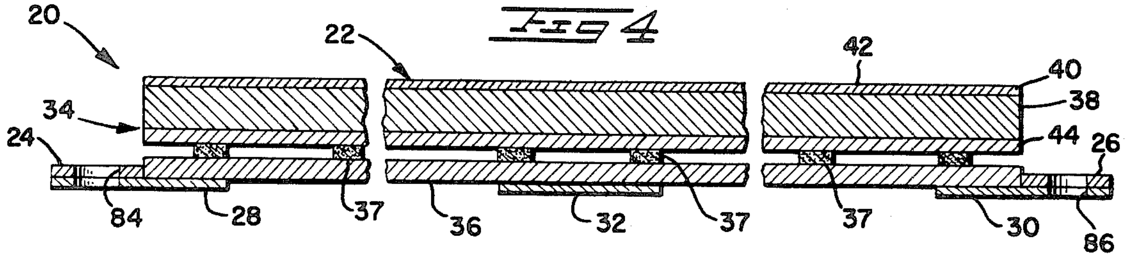
FIG. 4 is a section through the visible index strip roll of FIG. 3 taken substantially along line 4—4 of that Figure.

The butted together index strip assemblages 22 are oriented so that the index strips they contain extend transversely with respect to the lengthwise dimension of the roll indicated by reference character 27 in FIG. 3.

The perforated strips extend lengthwise of roll 20 and are joined to the index strip assemblages 22 at the edges or margins of the roll defined by the similarly oriented ends of the index strips with adhesively faced, flexible tapes 28 and 30. The latter are made from a relatively strong, readily available and relatively inexpensive material such as Mylar. The tapes 28 and 30 also join the butted index strip assemblages together into the unitary assembly or roll 20.

Typically, a third adhesively faced tape 32 of similar character spaced approximately mid way between the edges of the assemblages will be employed to help hold the visible index strip assemblages 22 together in the wanted, illustrated, abutted relationship.

Each of the exemplary visible index assemblages 22 making up visible index roll 20 includes a plurality of elongated, flexible index strips 34 which extend completely across a backing sheet 36 and are bonded to the backing sheet by spaced lines 37 of a releasable adhesive which has an adhesive strength with respect to said index strips and said backing sheet that is greater than the cohesive or internal strength of the adhesive so that the adhesive will rupture internally when an index strip 34 is detached from backing sheet 36. This leaves a strip which has clean edges and ends and is free of material torn from the backing sheet.

One suitable adhesive of this type is H. B. Fuller Company Product No. F-3117-X. Other adhesives of this character are commercially available and may be used instead, if desired. Also, the glue can be applied in a continuous layer or other pattern rather than in the illustrated pattern of parallel lines 37, if desired.

The index strips 34 of assemblages 22 may be made of any desired material such as a suitable plastic or the conventional paper covered wood veneer, and they can be of essentially any suitable construction including those disclosed in the patents listed above. However, they will preferably be of the novel, all paper construction disclosed in copending application Ser. No. 30,458 and shown in FIG. 4 herein. Those strips 34 are of three-ply construction and include a central ply 38, an outer or top ply 40 which provides an information receiving surface 42, and a third or bottom ply 44 to which the backing sheet 36 is bonded.

In one exemplary index strip of this type, outer or top ply 40 is an 0.004 inch thick bond. The central ply or core stock 38 is 0.022 inch thick International Paper Company Luxcell resin impregnated paper; and the third, bottom ply 44 is a 0.005 inch thick paper from Riegel Products Corporation.

The backing sheet 36 used with the just described strips is an 0.007 inch thick paper made by International Paper Company.

Luxcell is the name under which the cellulosic, resin impregnated, core stock materials described above and in U.S. Pat. No. 3,769,143 are marketed by International Paper Company.

The three plies 38, 40, and 44 of the strips are bonded together in face-to-face relationship by appropriate adhesives. Adhesives which are particularly suitable are H. B. Fuller Company products 2363 and 3555-EN.

The total thickness of the index strips may vary but will preferably be on the order of 0.03 inch to make them compatible with existing index strip supports such as those manufactured by Datastrip Corporation, Charlottesville, Va.

In addition, one or more of the papers making up index strips 34 can advantageously be of the type in which the paper fibers are for the most part (80 percent or more) oriented in one direction. In making assemblages 22, the ply or plies of this character are oriented so that the fibers will extend in the same direction as the longitudinal axes of the strips. It has been found that this provides maximum strength and, also, sufficient flexibility that the strips can be bent to the extent necessary to insert or fit them in a frame or support without exceeding their elastic limit.

The index strip assemblages 22 are made by bonding the several plies or laminae 38, 40, and 44 together and to backing sheet 36. The strips are then typically formed by scoring the resulting assembly along parallel lines—by using rotary slitters as described in U.S. Pat. No. 2,385,082 issued Sept. 18, 1945, to Hopkins, for example. The score lines must extend through the strips and can extend to or through the adhesive bonding the index strips 34 to backing sheet 36 or even into the backing sheet itself as long as the structural integrity of the latter is retained.

Referring again to the drawing, FIG. 4 also shows the relationship among the visible index strip assemblages 22; the perforated strips or ribbons 24 and 26 extending along the margins of the serially abutted array of index strip assemblages; and the adhesively faced tapes 28 and 30 by which the perforated strips 24 and 26 are joined to the assemblages of index strips.

The perforated ribbons 24 and 26; the adhesively faced tapes 28 and 30 by which they are joined to the visible index strip assemblages; and the centrally located, adhesively faced reinforcing tape 32 extend lengthwise in relation to the abutted visible index strip assemblages 22. The first-mentioned components are all furnished in running lengths sufficient to span a plurality of the visible index strip assemblages. They thereby join the several assemblages 22 into a continuous array or row possessing a high degree of structural integrity.

Also noteworthy is that the adhesively faced tapes 28 and 30 are sufficiently wide to span the perforated ribbons and also lap onto, and thereby join the ribbons to, the backing sheets 36 of the visible index assemblages. Consequently, the joining of the perforated ribbons to the assemblages does not in any way interfere with the removing of the index strips from the backing sheets to which they are attached.

In the embodiment of my invention illustrated in FIGS. 3 and 4, the flexible, perforated ribbons 24 and 26 are three-eighths of an inch wide; and they are made of an 0.009 inch thick Riegel paper. That this particular material is employed is not critical, however; and neither is the thickness of the ribbons.

Other papers, plastics, and still other flexible materials can also be employed as long as they have sufficient structural integrity to withstand whatever forces might be exerted on them by the registration device of the machine in which the wanted information is printed on the visible index strips.

Referring now to FIGS. 1 and 2, the exemplary, illustrated machinery for manufacturing visible index strip roll 20 has a station 46 equipped with cooperating press rolls and contrarotating feed rolls 48 and 50 at the right-hand side of the station and duplicate set-ups of feed and press rolls (not shown) at the left-hand side of the station.

Feed rolls 48 and 50 and their duplicates, all located downstream from the associated press rolls, engage the opposite, upper and lower surfaces of the artifact formed by the joined together index strip assemblages 22 and marginal strips 24 and 26.

As suggested in FIG. 2, the press rolls include, at locations corresponding to the opposite sides of the visible index strip roll being manufactured, upper press rolls 52 and 54 and a bottom press roll 56 arranged to rotate in the opposite direction from the upper press rolls.

The directions of rotation of the several press and feed rolls are indicated by arrows 58, 60, 62, and 64 in FIG. 1.

Referring still to that figure, the visible index strip assemblages are so oriented as they are fed into the nip 66 between upper and lower press rolls 52 and 56 and through the corresponding nip of the press roll set-up duplicated at the other edge of the assemblages that the index strips 34 extend at right angles to the direction of movement 68 of the assemblages.

As shown in FIG. 2, upper press roll 54 may be made somewhat larger in diameter than the associated upper press roll 52 to provide an exposed, inwardly facing, radially oriented, peripheral portion 69 for positioning and guiding the index strip assemblages as they pass through the nips between the upper and lower press rolls. This arrangement is also preferably duplicated at the left-hand side of station 46.

Simultaneously, the paper strips or ribbons 24 and 26 and the adhesively faced tapes 28 and 30 are fed to station 46. One of the reels for the paper strips is identified by reference character 70 in FIG. 1 and one of the reels of tape by reference character 72. These reels are duplicated at the other opposite side of station 46.

As shown in FIG. 2, tape 26 passes through the nip 73 between upper press roll 54 and lower press roll 56, juxtaposing it to the margins 74 at the right-hand side of successive index strip assemblages. Ribbon 24 is similarly positioned relative to the margins formed by the left-hand edges of successive index strip assemblages 22.

The tapes 28 and 30 pass beneath the backing sheets 36 and flexible ribbons 24 and 26, and the adhesive surfces of the tapes face those components of roll 20.

As suggested by FIG. 2, the adhesively faced surfaces 75 of the illustrated, exemplary tapes 28 and 30 are consequently pressed against ribbons 24 and 26 and against the corresponding marginal portions of backing sheets 36 of successively fed visible index strip assemblages as the latter, the ribbons, and the flexible tapes move through the nips 66 and 73 between the upper and lower press rolls.

At the same time, a third set of rolls (not shown) similarly presses the third, centrally located reinforcing tape 32 against the backing sheets of the index strip assemblages.

The continuous assembly thus formed is transferred by feed rollers 48 and 50 to a second station 76 where a conventional, reciprocating feed mechanism 78 advances the assembly in increments of selected length to conventional hole punches in the paths of flexible ribbons 24 and 26 (one of these two hole punches is identified by reference character 80 in FIG. 1). The perforations thereby made in ribbons 24 and 26 for the registration device of a printing machine adapted to handle the visible index roll are identified by reference characters 84 and 86 in FIGS. 3 and 4.

As shown in FIG. 1, slack is left in the completed assembly as it passes from station 46 to station 76, forming a manufacturing loop 87. This insures that the reciprocating feed mechanism 78 at station 76 will not pull the assembly apart as it feeds the latter to the hole punches.

The second work station 76 and the equipment employed there can of course be eliminated by substituting perforated ribbons for those identified by reference characters 24 and 26. This may, on the other hand, introduce complexities into the manufacturing process because of the need for precisely registering the perforations in the marginal ribbons with the index strips.

The manufacturing operation is completed by winding the assembly into a roll on a conventional reel or spindle 88 (see FIG. 1).

Those discussed above are merely representative of the uses to which the principles of the present invention may be put.

For example, rolls of index strips with a backing sheet whih is ruptured to separate the strips—see U.S. Pat. No. 1,594,112 issued July 27, 1926, to Powell—can more economically be made in accord with thoe principles than by the processes described in the Deinlein et al and Fleischhauer patents identified above because marginal perforations are provided in relatively inexpensive strips of paper or the like rather than in the relatively costly, wood veneer as in the patented process.

Figure 5:
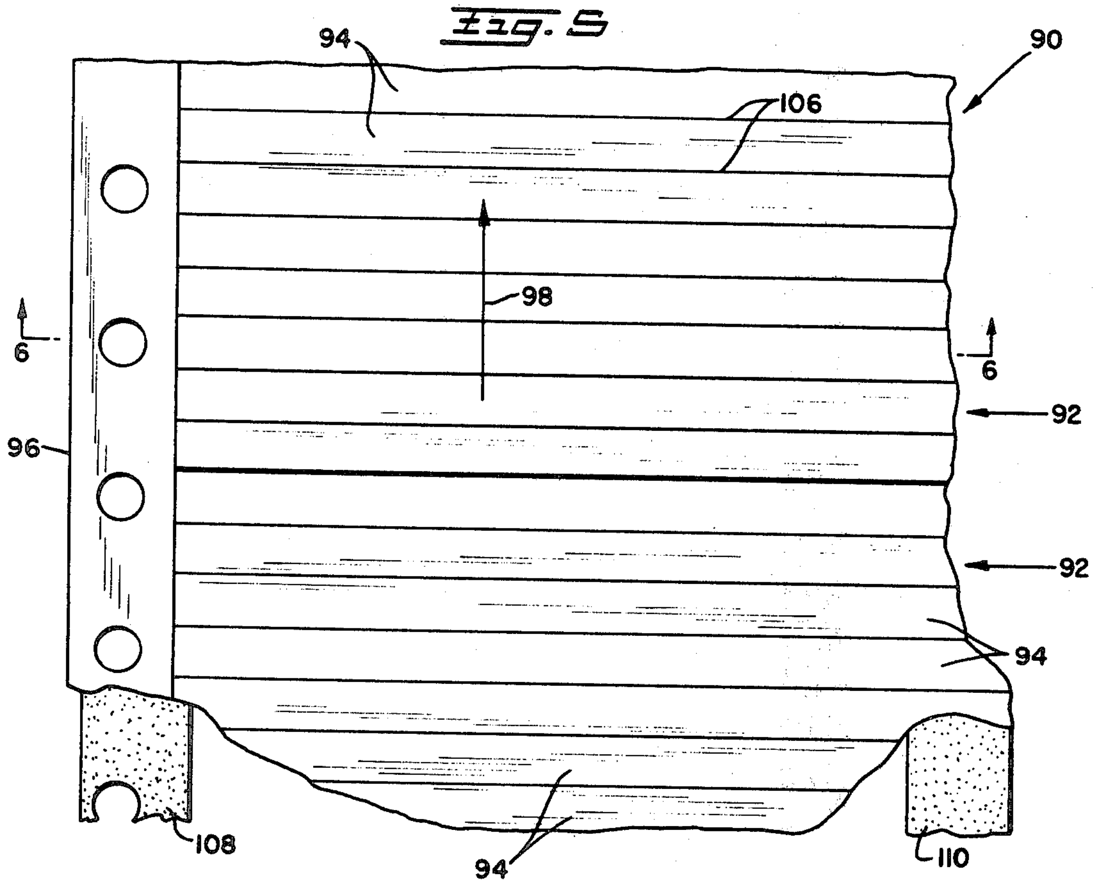
FIG. 5 is a view similar to FIG. 3 of a second form of visible index strip roll embodying the principles of the present invention.
Figure 6:
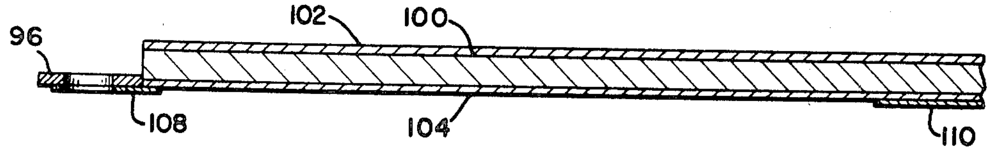
FIG. 6 is a section through the visible index strip roll of FIG. 5, taken substantially along line 6—6 of the latter Figure.

Referring again to the drawing, FIGS. 5 and 6 illustrate a visible index strip roll 90 thus manufactured from butted together, sheets 92 of visible index strips 94 as disclosed in the above-identified Powell patent. Index strip roll 90 also has perforated, flexible marginal ribbons 96 (only one of which is shown) of the character and for the purposes discussed above.

As in the case of roll 20, the butted together sheets 92 of index strips are oriented so that the index strips 94 extend transversely with respect to the lengthwise dimension of the roll (indicated by reference character 98).

In this embodiment of my invention, each sheet 92 of index strips has a core 100 of Luxcell, wood veneer, or other suitable material faced with a top ply 102 of the character described above and a bottom ply or backing sheet 104 of tissue thickness.

The top ply 102 and core 100 of the sheet are scored through along the lines indicated by reference character 106 in FIG. 5 to the backing sheet or bottom ply 104. This defines the index strips 94 while the intact backing sheet maintains them as a cohesive assemblage. As suggested above, individual index strips are subsequently separated by rupturing the backing sheet 104.

The perforated marginal strips 96 extend lengthwise of roll 90. They are joined to the sheets 92 of index strips at the edges or margins of the roll defined by similarly oriented ends of the index strips with adhesively faced, flexible tapes 108 of the character described above which lap onto the backing sheets 104 of the rolls (one tape is shown in FIG. 6). These tapes also join the butted sheets 92 of index strips together into the unitary roll 90.

Typically, as in the case of index roll 20, a third, adhesively faced tape 110 of similar character spaced approximately mid way between the edges of sheets 92 will be employed to help hold those sheets together in the wanted, illustrated, abutted relationship.

In the index strip roll construction illustrated in FIGS. 5 and 6, the strips must be peeled from tapes 108, or 108 and 110, when the backing sheet 104 is ruptured to separate the strips. This is somewhat more cumbersome than removing the index strips from the roll 20 shown in FIGS. 3 and 4; but it can nevertheless be accomplished with fair alacrity.

To further illustrate the scope which I consider my invention to have, I point out that the perforations in the marginal strips of the index rolls can be provided for purposes other than registration in a printing machine.

For example, the top ply 40 of the index strip construction illustrated in FIGS. 3 and 4 can advantageously be supplied in preprinted form. In this case, the sheets of index strips minus the top ply can be joined and the marginal strips added and the top ply then bonded to the resulting assemblage in an appropriate laminater. In this case, the perforations in the marginal strips can be utilized to insure proper registration of the incipient roll and the preprinted top ply in the laminater.

The invention may also be embodied in many other specific forms without departing from the spirit or essential characteristics thereof. The present embodiments are therefore to be considered in all respects as illustrative and not restrictive, the scope of the invention being indicated by the appended claims rather than by the foregoing description; and all changes which come within the meaning and range of equivalency of the claims are therefore intended to be embraced therein.

What is claimed and desired to be secured by Letters Patent is:

1. A method of manufacturing a visible index strip roll, comprising the steps of: feeding serially to a work station assemblages composed of a backing sheet and a plurality of separate and independent, elongated index strips fixed in juxtaposed, face-to-face relationship to said backing sheet, which may constitute one outer ply of the visible index strips, said assemblages being oriented as they arrive at said station with said strips extending at right angles to the direction of movement of the assemblages; simultaneously feeding flexible ribbons through said station on opposite sides of said index strip assemblages and juxtaposed thereto in the direction of movement of the assemblages; and joining said ribbons to the backing sheets of said index strip assemblages by feeding to said work station in locations spanning said ribbons and those portions of the index strip assemblage backing sheets thereadjacent an adhesively faced tape of flexible material.

2. A method of manufacturing a visible index strip roll, comprising the steps of: feeding serially to a work station assemblages each composed of a backing sheet and a plurality of separate and independent, elongated index strips fixed in juxtaposed, face-to-face relationship to said backing sheet, which may constitute one outer ply of the visible index strips, said assemblages being oriented as they arrive at said station with said strips extending at right angles to the direction of movement of the assemblages; simultaneously feeding flexible ribbons which are independent of said assemblages through said station on opposite sides of said index strip assemblages and juxtaposed thereto in the direction of movement of the assemblages; and mechanically joining sid ribbons to the backing sheets of said index strip assemblages by feeding to said work station in those locations spanning each of said ribbons and those portions of the index strip assemblage backing sheets thereadjacent an adhesively faced tape of flexible material.

3. A method of making a visible index strip roll as defined in claim 1 or in claim 2 wherein said work station comprises a roll pair and wherein said index strip assemblages, said flexible ribbons, and said tape are fed through the nip between the rolls.

4. A method of making a visible index strip roll as defined in claim 1 or in claim 2 wherein said backing sheet is discardable and said index strips are removably attached thereto.

5. A method of making a visible index strip roll as defined in claim 1 or in claim 2 wherein said backing sheet forms an outer ply of said index strips and is rupturable to separate the index strips.

6. A method of making a visible index strip roll as defined in claim 1 or in claim 2 in which, after the flexible ribbons are joined to the backing sheets of the index strip assemblages, perforations engageable by the registration device of a subsequent process machine are formed in said flexible ribbons at intervals therealong.

7. A process of making a visible index strip roll as defined in claim 6 wherein said process machine has a printing capability.

* * * * *